(12) United States Patent
Das et al.

(10) Patent No.: US 9,321,697 B2
(45) Date of Patent: Apr. 26, 2016

(54) RECOMBINANT NITROGEN FIXING MICROORGANISM AND USES THEREOF

(71) Applicant: Department of biotechnology ministry of science & technology+Jawaharlal nehru university, New Delhi (IN)

(72) Inventors: Hirendra Kumar Das, New Delhi (IN); Umesh Kumar Bageshwar, College Station, TX (US); Madhulika Srivastava, New Delhi (IN)

(73) Assignee: Department of Biotechnology Ministry of Science & Technology+Jawaharlal Nehru University, New Delhi (IN)

( * ) Notice: Subject to any disclaimer, the term of this patent is extended or adjusted under 35 U.S.C. 154(b) by 0 days.

(21) Appl. No.: 14/382,340

(22) PCT Filed: Mar. 4, 2013

(86) PCT No.: PCT/IN2013/000123
§ 371 (c)(1),
(2) Date: Sep. 2, 2014

(87) PCT Pub. No.: WO2013/132518
PCT Pub. Date: Sep. 12, 2013

(65) Prior Publication Data
US 2015/0128670 A1 May 14, 2015

(30) Foreign Application Priority Data

Mar. 3, 2012 (IN) .............................. 465/DEL/2012

(51) Int. Cl.
| | |
|---|---|
| C05F 11/08 | (2006.01) |
| C12N 1/20 | (2006.01) |
| C12N 15/00 | (2006.01) |
| C12N 15/74 | (2006.01) |
| C07K 14/195 | (2006.01) |
| C12N 15/90 | (2006.01) |

(52) U.S. Cl.
CPC ............... *C05F 11/08* (2013.01); *C07K 14/195* (2013.01); *C12N 15/902* (2013.01); *C12N 2800/90* (2013.01)

(58) Field of Classification Search
None
See application file for complete search history.

(56) References Cited

U.S. PATENT DOCUMENTS

| 6,548,289 B1 | 4/2003 | Beynon et al. |
| 2006/0270555 A1 | 11/2006 | Okuyama et al. |

FOREIGN PATENT DOCUMENTS

| DE | 102007002040 | 7/2008 |
| EP | 0339830 A2 | 11/1989 |
| GB | 2259302 A | 3/1993 |
| WO | 03071976 | 9/2003 |
| WO | 2012042547 | 4/2012 |

OTHER PUBLICATIONS

F. Reyes-Ramirez et al: "Mutant Forms of the Azotobacter vinelandii Transcriptional Activator NifA Resistant to Inhibition by the NifL Regulatory Protein", Journal of Bacteriology, vol. 184, No. 24, Dec. 15, 2002, pp. 6777-6785, XP055070122, ISSN: 0021-9193, DOI:10.1128/JB. 184.24.6777-6785.2002 the whole document.
McManus P 5 et al: "Antibiotic use in 1-20 plant agriculture", Annual Review of Phytopathology, Annual Reviews Inc, US, vol. 40, Jan. 1, 2002, pp. 443-465, XP002442836, ISSN: 0066-4286, DOI:10. 1146/ANNUREV. PHYTO.40. 120301.093927 abstract.
Palmeros B et al: "A family of removable 1-20 cassettes designed to obtain antibiotic-resistance-free genomic modifications of *Escherichia coli* and other bacteria", Gene, Elsevier, Amsterdam, ML, vol. 247, No. 1-2, Apr. 1, 2000, pp. 255-264,XP004 19 65 72 ISSN: 0378-1119, DOI:10. 1016/S0378-1119(00)00075-5 the whole document.
Cherepanov P P et al: "Gene disruption in 1-20 *Escherichia coli*: Tc<R> and Km<R>cassettes with the option of Flp—catalyzed excision of the antibiotic-resistance determinant", Gene, Elsevier, Amsterdam, ML, vol. 158, No. 1, Jan. 1, 1995, pp. 9-14, XP004206666, ISSN: 0378-1119, DOI :10.1016/0378-1119(95)00193-A the whole document.
Colnaghi Rita et al: "Strategies for increased ammonium production in free—living or plant associated nitrogen fixing bacteria", Plant and Soil, vol. 194, No. 1-2, Jul. 1997, pp. 145-154.XP002700267, ISSN: 0032-079X the whole document.
Maldonado Rafael et al : "Gene dosage analysis in Azotobacter vinelandii", Genetics,vol. 132, No. 4, 1992, pp. 869-878,XPOO2700268,ISSN: 0016-6731 abstract.
Bali et al. App. Env. Microbiol. vol. 58, 1992, pp. 1711-1718.
Bergersen F. J: 'Methods for evaluating biological nitrogen fixation', 1980, John Wiley and Sons.
Brewin et al. J. Bacteriol. vol. 181, 1999, pp. 7356-7362.
F. M. Ausubel; R. Brent; R.E. Kingston; D.D. Moore; J.G. Seidman; J.A. Smith; K. Struhl: 'Current Protocols in Molecular Biology', 1987, Greene Publishing Associates/Wiley Interscience.
I.R. Kennedy et al. Soil Biology & Biochemistry vol. 36, 2004, pp. 1229-1244.
Martinez-Argudo et al. J Bacteriol. vol. 186, No. 3, 2004, pp. 601-610.
Punita et al. J. Bacteriol vol. 171, 1989, pp. 3133-3138.
Raina et al. Mol. Gen. Genet. vol. 237, 1993, pp. 400-406.
T. Maniatis; E. F. Fritsch; J. Sambrook: 'Molecular Cloning: a laboratory manual', 1982, Cold Spring Harbor Laboratory.
PCT/IN2013/0000123, International Search Report, issued Jul. 18, 2013.

*Primary Examiner* — Iqbal H Chowdhury
(74) *Attorney, Agent, or Firm* — Mark M. Friedman

(57) ABSTRACT

A recombinant microorganism is provided herein, in particular, a recombinant microorganism of the Azotobacteraceae family. The recombinant *Azotobacter* microorganism is capable of fixing atmospheric nitrogen continuously in the presence of oxygen and externally fixed nitrogen sources. The present invention further provides a process for production of the recombinant microorganism and a composition comprising the recombinant microorganism for use as biofertilizers and/or for use in the preparation of a fertilizer composition. The recombinant microorganism produced by this invention is an environmental friendly, highly beneficial microorganism.

16 Claims, 2 Drawing Sheets

RECOMBINANT NITROGEN FIXING MICROORGANISM AND USES THEREOF

FIELD OF INVENTION

The present invention relates to the field of microbiology and genetic engineering. The present invention relates to a recombinant microorganism, in particular it is related to recombinant *Azotobacter* capable of fixing atmospheric nitrogen in the presence of fixed nitrogen, oxygen or a combination thereof.

BACKGROUND OF THE INVENTION

Biological nitrogen fixation (BNF) occurs when atmospheric nitrogen is converted to ammonia by an enzyme called nitrogenase. Only some selected microorganisms are able to transform nitrogen from the abundant gaseous form to usable combined nitrogen compounds. Microorganisms that fix nitrogen are called diazotrophs. Enzymes responsible for nitrogenase action are very susceptible to destruction by oxygen. The nif genes are responsible for the coding of the nitrogenase proteins and other proteins related to and associated with the fixation of atmospheric nitrogen into a form of nitrogen available to plants. The nif genes have both positive and negative regulators. Besides the nitrogenase enzyme, the nif genes also encode a number of regulatory proteins involved in nitrogen fixation. The expression of nif genes is induced as a response to low concentrations of fixed nitrogen and low oxygen concentrations (the low oxygen concentrations are actively maintained in the root environment). In most of the nitrogen fixing microorganisms, activation of transcription of the nif genes is done by the NifA protein. When there is not enough fixed nitrogen available for the use of the nitrogen fixing microorganisms, NifA expression is initiated from the native promoter of the nifA gene, while the NifA protein in turn leads to activation of the remaining nif genes transcription. If there is sufficient amount of reduced nitrogen or if oxygen is present, nifA gene promoter is not activated and no NifA protein expression takes place. On the other hand, another protein, NifL, is activated in presence of reduced nitrogen or oxygen, and this activated NifL inhibits NifA protein activity by interacting with it, resulting in the inhibition of the formation of nitrogenase and all other accessory proteins necessary for nitrogen fixation.

Nitrogen fixation in the free-living, aerobic, heterotrophic, diazotrophic gram negative soil bacterial genus, *Azotobacter* spp is regulated by the nifLA operon. Here also NifA protein activates the transcription of all the nif genes, while NifL protein antagonizes the transcriptional activator NifA in response to fixed nitrogen and molecular oxygen. The expression of the nif operons of *Azotobacter* is mediated by sigma-54 transcription factor, rather than the more common sigma-70 transcription factor. A typical characteristic of sigma 54 transcription factors is the requirement of an activator that must bind to DNA at a site about 100 or more bases upstream of the promoter. The nifA gene is present in *Azotobacter* in the nifLA operon and is located distal to the promoter of nifLA operon. The nifL gene is also present in *Azotobacter* in the nifLA operon and is located proximal to the promoter of nifLA operon. Here also, NifL is the negative regulator, which is activated in presence of oxygen or ammonia. NifL inactivates NifA by interacting with it. In addition to NifA, the promoter of the native nifLA operon is also repressed by oxygen and ammonia. The nifLA operon serves as the master regulatory operon for the entire process of nitrogen fixation. Raina et al. [1993, *Mol. Gen. Genet.* 237: 400-406] has fully characterized the nifL gene of *Azotobacter vinelandii* and has elucidated its regulation. Unlike in the case of *Klebsiella pneumoniae*, the expression of the nif LA operon in *Azotobacter vinelandii* is not autogenously regulated. Bali et al. [1992, *App. Env.* Microbiol. 58: 1711-1718] inserted an antibiotic resistance cassette upstream of nifA of *Azotobacter vinelandii* and observed enhanced nitrogen fixation and excretion. Brewin et al. [1999, *J. Bacteriol.* 181: 7356-7362] studied ammonium excretion in nifL mutants of *Azotobacter vinelandii* obtained by insertion of antibiotic resistance cassette and concluded that ammonium is excreted from the cell passively. In *Azotobacter vinelandii*, current evidence suggests that NifL controls the activity of NifA by a relatively stable protein-protein interaction that is modulated by redox changes, ligand binding, and interactions with other signal transduction proteins and membrane components. *Azotobacter vinelandii* NifL contains a conserved histidine residue found in the transmitter domains of histidine kinases, suggesting that this NifL might employ a classical phosphoryl transfer mechanism to communicate environmental signals to NifA. However, replacement of this conserved histidine by a number of other amino acids does not disable signal transduction. Furthermore, NifL is competent to inhibit NifA in vitro in the absence of ATP, and signal transduction requires stoichiometric protein-protein interactions between the two regulatory proteins (Martinez-Argudo et al., *J Bacteriol.*, 2004, 186(3): 601-610).

In both cereals and non-cereal crops, there is a need to supply extra fixed nitrogen by industrially-fixed nitrogen or biologically fixed nitrogen to supplement nitrogen availability in the soil. Nitrogen released to the available pool by mineralization is expected to depend on the amount of soil-nitrogen removed in the harvested produce, leaching of inorganic nitrogen (e.g. $NO_3^-$—N) to groundwater, the magnitude of denitrification of soil-nitrogen as $N_2O$ or $N_2$, the extent and duration of immobilization of N and its rate of remobilization in the soil biomass (I. R. Kennedy et al., 2004, Soil Biology & Biochemistry 36: 1229-1244). Inoculant biofertilizers, particularly nitrogen-fixing bacterial diazotrophs, can help ensure that the supply of nutrients contributing to optimized yield is maintained. However, in the presence of chemical nitrogenous fertilizers, there is no biological nitrogen fixation, because the ammonium generated by the chemical fertilizer switches off the nifLA operon and therefore, subsequently all the nif operons.

U.S. Pat. No. 6,548,289 describes a method for increasing the rate of conversion of atmospheric nitrogen into ammonia in the genus *Rhizobium*, by increasing the intracellular level of the activator protein NifA, by introducing a plasmid containing the nifA gene under an inducible or a constitutive promoter. The problem with this method is that the plasmid has an antibiotic resistance gene, which is undesirable from environmental considerations. Besides, the presence of the antibiotic in the medium or the soil would be essential for stable maintenance of the plasmid inside the bacteria. Thus, continuous selection pressure is required to maintain the stability of the plasmids in the bacteria.

United States Patent Application 20060270555 describes transformation of root nodule bacteria with a catalase gene leading to enhanced nitrogen-fixation ability, a preparation for leguminous crops containing the root nodule bacteria as an active ingredient, and a method of cultivating leguminous crops comprising contacting seeds of crops with the transformed bacteria.

Recombinant microorganisms showing uninterrupted biological nitrogen fixation has been investigated by other researchers by inserting an antibiotic resistance cassette into the nifL gene. However, such microorganisms harboring the antibiotic resistance genes are not acceptable for agricultural use due to environmental concerns. There is a dire need to reduce costs associated with chemical fertilizers and reduce the contribution of these chemical fertilizers to environmental pollution. Therefore, it is highly imperative that novel and inventive products and processes should be developed such that the agricultural costs are reduced with a beneficial effect on the environment.

SUMMARY OF THE INVENTION

One aspect of the present invention provides a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene.

Another aspect of the present invention provides a process for producing a recombinant microorganism, wherein the process comprises (a) inserting a disrupted nifL gene and a nifA gene with the native promoter into the chromosome of a microorganism through homologous recombination with a recombinant DNA molecule comprising a disrupted chromosomal nifL gene, a nifA gene with native promoter and an antibiotic resistance marker gene to obtain a transformed microorganism, wherein the nifL gene is disrupted by insertional mutagenesis, deletion of genomic DNA, targeted gene disruption or introduction of a genomic or episomal vector, and (b) inserting a heterologous constitutive promoter to the upstream of the nifA gene of the transformed microorganism through homologous recombination with a recombinant DNA molecule comprising the constitutive heterologous promoter to obtain a recombinant microorganism comprising a disrupted nifL gene and a nifA gene operably linked to the heterologous constitutive promoter, wherein the recombinant microorganism is capable of fixing atmospheric nitrogen in presence of fixed nitrogen and oxygen and does not comprise antibiotic resistance marker gene.

*Azotobacters* are known to have multiple chromosomes [Punita et al J. Bacteriol 171(1989) 3133-3138]. This two-step procedure was essential to adopt so as to exert strong selection pressure for making sure that the mutation is transmitted to each and every copy of the chromosome, as otherwise reversion would take place after some time.

BRIEF DESCRIPTION OF ACCOMPANYING DRAWINGS

FIG. 1 shows the following elements:

FIG. 1A shows the partial restriction map of the 7.5 kb Bam HI fragment from *Azotobacter chroococcum* CBD15 which contains regions homologous to nifL and nifA of *Azotobacter vinelandii* UW, cloned in the Bam HI site of pUC7. This construct is denoted as pCL6. The restriction enzyme sites are denoted as E: EcoRI; B: BamHI; Nc: NcoI; Sa: SacII; S: SalI; K: KpnI. The restriction sub-fragments that hybridize with nifL and nifA of *Azotobacter vinelandii* UW are underlined.

OBJECTS OF THE INVENTION

Figure 1:
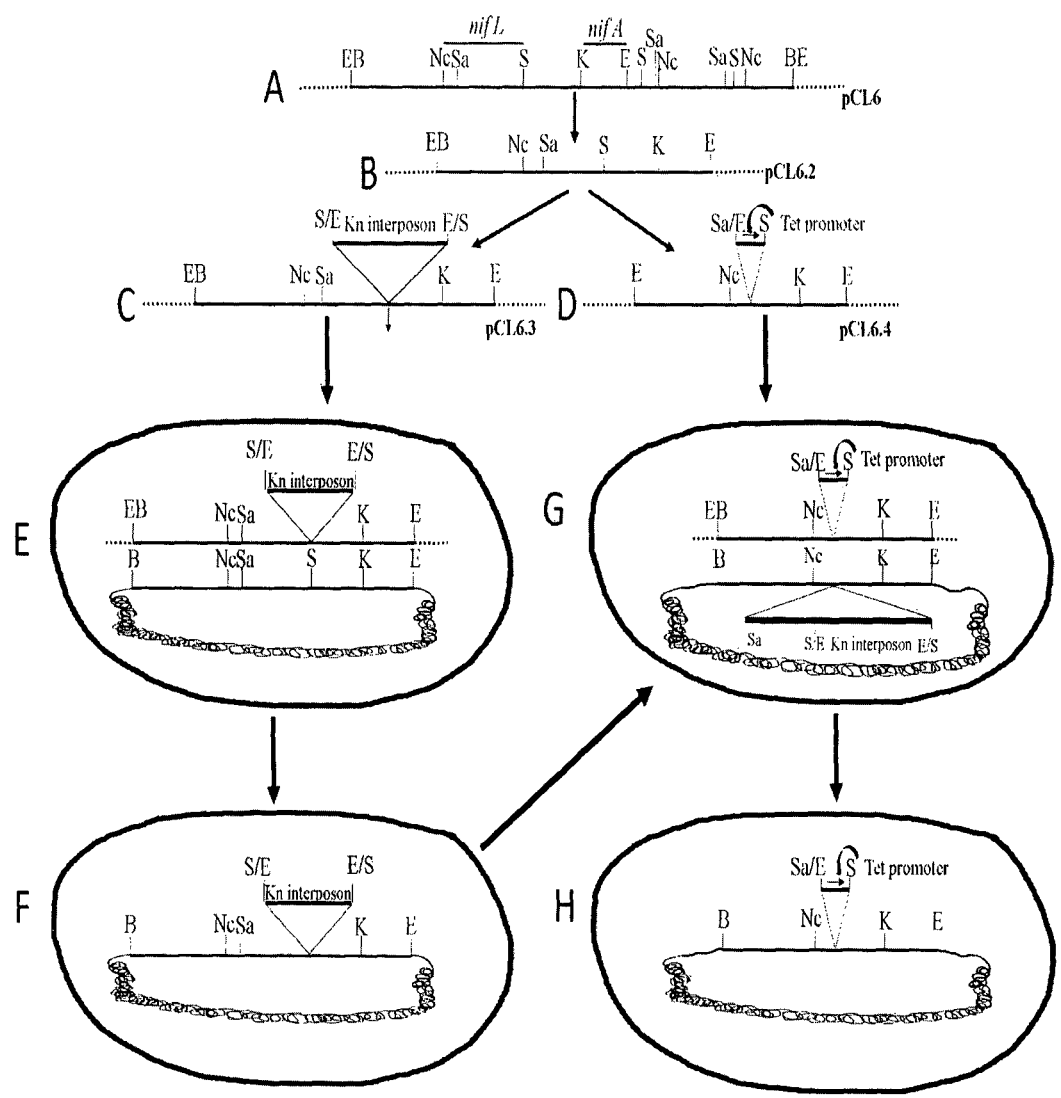
FIG. 1B shows the 4.8 kb EcoRI fragment from pCL6 containing the regions homologous to nifL and nifA of *Azotobacter vinelandii* UW cloned in pUC7. This construct is denoted as pCL6.2.
FIG. 1C shows the 2.0 kb EcoRI fragment from pHP45 ΩKm containing the interposon ΩKm inserted in place of the Sal I sites of pCL6.2. This construct is denoted as pCL6.3.
FIG. 1D shows the deletion of a 1.1 kb DNA fragment around the Sal I sites from pCL6.2 and insertion of 0.38 kb EcoRI-BamHI fragment containing the pBR322 constitutive promoter into the same site. This construct is denoted as pCL6.4.
FIG. 1E shows the insertion of the construct pCL6.3 into *Azotobacter chroococcum* CBD15 by electroporation.
FIG. 1F shows the integration of the ΩKm interposon into the nifL gene in the genome of *Azotobacter chroococcum* CBD15 via homologous recombination.
FIG. 1G shows the introduction of the construct pCL6.4 harbouring the ΩKm interposon in the nifL gene, by electroporation into *Azotobacter chroococcum* CBD15.
FIG. 1H shows the replacement of the 1.1 kb DNA fragment around the Sal I sites of the nifL gene comprising the ΩKm interposon in the genome of *Azotobacter chroococcum* CBD15 with EcoRI-BamHI fragment of the pCL6.4 construct containing the pBR322 constitutive promoter, via homologous recombination.

An object of the present invention is to provide a recombinant microorganism capable of converting atmospheric nitrogen into biological fixed nitrogen in the presence of fixed nitrogen and oxygen.

Another object of the present invention is to provide a recombinant microorganism with increased capacity to fix atmospheric nitrogen in the presence of fixed nitrogen, and oxygen, wherein the recombinant microorganism does not comprise any antibiotic resistance marker gene.

Another object of the present invention is to provide crop plant inoculants and biofertilizer composition comprising the recombinant microorganism of the present invention capable of continuous biological nitrogen fixation in presence of fixed nitrogen and oxygen thereby increasing the yield of the crop plants and reducing the degradation of soil.

Another object of the present invention is to provide a way of reducing the application of chemical nitrogenous fertilizers in agriculture and reducing environmental pollution.

DETAILED DESCRIPTION OF THE INVENTION

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

In accordance with the present invention, there may be employed conventional molecular biology, microbiology and recombinant DNA techniques within the skill of the art. Such techniques are fully explained in the literature (T. Maniatis, E. F. Fritsch and J. Sambrook; 1982, *Molecular Cloning: a laboratory manual*. Cold Spring Harbor Laboratory; F. M. Ausubel, R. Brent, R. E. Kingston, D. D. Moore, J. G. Seidman, J. A. Smith, and K. Struhl, 1987, *Current Protocols in Molecular Biology*, Greene Publishing Associates/Wiley Interscience, New York).

DEFINITIONS

For convenience, before further description of the present invention, certain terms employed in the specification, examples and appended claims are provided here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a," "an" and "the" are used to refer to one or to more than one (i.e., to at least one) of the grammatical object of the article.

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

It is not intended to be construed as "consists of only."

The term "including" is used to mean "including but not limited to".

The term "nucleic acid" or "recombinant nucleic acid" refers to polynucleotides such as deoxyribonucleic acid (DNA), and, where appropriate, ribonucleic acid (RNA).

The polynucleotides described in the present description include "genes" and nucleic acid molecules described include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a recombinant DNA molecule is introduced into a host cell. Transformation (or transduction, or transfection), can be achieved by any one of a number of means including electroporation, microinjection, biolistics (or particle bombardment-mediated delivery), or *Agrobacterium*-mediated transformation.

Those of skill in the art will recognize that, due to the degenerate nature of the genetic code, a variety of DNA compounds differing in their nucleotide sequences can be used to encode a given amino acid sequence of the disclosure. The native DNA sequence encoding the biosynthetic enzymes described are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate embodiments of the disclosure.

The disclosure provides nucleic acid molecules in the form of recombinant DNA expression vectors or plasmids. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions).

The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

The term "promoter" refers to a DNA sequence capable of controlling the expression of a coding sequence or functional RNA. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters".

The term "operably linked" refers to the association of nucleic acid sequences on a single nucleic acid fragment so that the function of one is affected by the other. For example, a promoter is operably linked with a coding sequence when it is capable of affecting the expression of that coding sequence. Coding sequences can be operably linked to regulatory sequences in sense or antisense orientation.

The present invention is not to be limited in scope by the specific embodiments described herein, which are intended for the purposes of exemplification only. Functionally-equivalent products, compositions, and methods are clearly within the scope of the invention, as described herein.

An *Azotobacter* mutant showing constitutive nitrogen fixation would be useful as biofertilizers. Freeing all the genes involved in nitrogen fixation from any negative regulation should, therefore, lead to enhanced biological nitrogen fixation, even in the presence of ammonium or other fixed nitrogen, so that chemical fertilizers and bacterial fertilizers can be used together.

The present invention provides a recombinant microorganism capable of fixing atmospheric nitrogen in presence of fixed nitrogen and oxygen, wherein the chromosome of the microorganism comprises a disrupted nifL gene, a nifA gene operably linked to a constitutive heterologous promoter and does not comprise any antibiotic resistance marker gene, wherein the nifL gene is disrupted by insertional mutagenesis. The recombinant microorganism of the present invention also does not contain any other external genes like toxic genes that are harmful to the environment. The desired characteristics in the recombinant microorganism are obtained through manipulation of its chromosome and without the necessity of maintaining a plasmid.

The present invention also provides the polynucleotide of nifL gene having the nucleotide sequence as set forth in SEQ ID NO: 1 (GenBank: X70993.1) and encoding the amino acid sequence as set forth in SEQ ID NO: 2 and the nucleotide sequence as set forth in SEQ ID NO: 3.

The present invention also provides the polynucleotide of nifA gene having the nucleotide sequence as set forth in SEQ ID NO: 4 (GenBank: Y00554.1) and encoding the amino acid sequence as set forth in SEQ ID NO: 5.

The nifLA operon serves as the master regulatory operon for the entire process of nitrogen fixation in microorganisms. The native promoter for nifA gene is an inducible promoter which is regulated by the presence of fixed nitrogen and oxygen. The inventors found a surprising and unexpected result when they manipulated the chromosomal, nifLA operon, a two-component regulatory system, by disrupting the negative regulatory component by partial deletion of nifL, and operably linking the positive component, nifA, under a constitutive heterologous promoter for continuous expression in a free-living, diazotrophic microorganism. It was unexpectedly found that the recombinant microorganism does not comprise any antibiotic resistance marker gene and there was successful, uninhibited continuous expression of the nitrogen-sensitive NifA transcription activator which increased the level of biological nitrogen fixation in the recombinant microorganism. The recombinant microorganism was also found to produce and excrete a high level of ammonia compared with the non-recombinant microorganism. The use of a constitutive promoter renders the recombinant microorganism very efficient in fixing the atmospheric nitrogen. The disruption of nifL by partial deletion renders the reversion to an active negative regulatory component impossible, and thus makes the recombinant microorganism very stable. The recombinant microorganism such as recombinant Azotobacter having Accession number MTCC 5679 so obtained is an ideal biofertilizer component as it does not comprise any antibiotic resistance marker gene or any other external genes like Bt genes, or any toxic genes.

The present invention also provides a process for producing a recombinant microorganism capable of fixing atmospheric nitrogen in presence of fixed nitrogen and oxygen, wherein the process comprises (a) inserting a disrupted nifL gene and a nifA gene with the native promoter into the chromosome of a microorganism through homologous recombination with a recombinant DNA molecule comprising a disrupted chromosomal nifL gene, a nifA gene with native promoter and an antibiotic resistance marker gene to obtain a transformed microorganism, wherein the nifL gene is disrupted by insertional mutagenesis, deletion of genomic DNA, targeted gene disruption or introduction of a genomic or episomal vector and (b) inserting a heterologous constitutive promoter to the upstream of the nifA gene of the transformed microorganism through homologous recombination with a recombinant DNA molecule comprising a constitutive heterologous promoter to obtain a recombinant microorganism comprising a disrupted nifL gene and a nifA gene operably linked to the heterologous constitutive promoter, wherein the recombinant microorganism is capable of fixing atmospheric nitrogen in presence of fixed nitrogen and oxygen and does not comprise antibiotic resistance marker gene.

The process of the present invention comprises a novel process for the transformation of the microorganism through homologous recombination, wherein the chromosome of the recombinant microorganism comprises a disrupted nifL gene, a nifA gene operably linked to a constitutive heterologous promoter and does not comprise any antibiotic resistance marker gene. Thus, the recombinant microorganism produced by the process of the present invention is capable of fixing atmospheric nitrogen in a continuous manner and is not under the control of external regulators. The principle underlying the present invention should be applicable to all nitrogen fixing microorganisms, particularly where a two-component regulation is employed via a positive and a negative regulatory element.

In the present invention, deletion of a part of the nifL gene of Azotobacter chroococcum CBD15, a strain isolated from the soil at Indian Agricultural Research Institute, Delhi, India, was performed. A DNA fragment containing the constitutive tet promoter isolated from the plasmid pBR322 was inserted upstream of nifA of Azotobacter chroococcum CBD15 comprising the disrupted nifL gene. This newly created deletion mutant strain does not comprise antibiotic resistance marker gene and has been designated as Azotobacter chroococcum HKD15. The recombinant microorganism has been submitted at the MTCC, IMTECH, India. The Accession No. for the strain is MTCC 5679. The two-step strategy of first disrupting the nifL gene by inserting an interposon and selecting for a nif-minus phenotype (absence of ability to fix atmospheric nitrogen) followed by replacing the interposon disrupted nifL gene with a partially deleted nif L gene and a heterologous constitutive promoter, to drive the positive regulatory element nifA resulting in a nif-plus phenotype (presence of ability to fix atmospheric nitrogen) is novel and not obvious.

In the present invention, the microbial DNA from Azotobacter chroococcum CBD15 is digested with restriction enzyme BamHI to obtain a genomic fragment comprising the nifL and the nifA genes. The nifA genes are identified and isolated on the basis of homology with the nifA and nifL genes already known in the art. A 7.5 kb genomic fragment comprising the nifL and the nifA genes is isolated on the basis of homology with the nifA and nifL genes of Azotobacter vinelandii UW (FIG. 1A). This 7.5 Kb genomic fragment is cloned into pUC7 vector and subjected to further restriction to obtain a 4.8 kb genomic fragment comprising the nifL and the nifA genes. This 4.8 kb fragment is cloned into pUC7 vector and the construct was designated as pCL6.2 (FIG. 1B). The pCL6.2 construct further comprises the 'second' antibiotic resistance marker gene (Ampicillin, Amp+) and is used for further transformation experiments.

Any vector that is stably replicated in any host cell for production of the constructs desired comprising the nifL and nifA genes of interest, but are unstable and do not replicate in the microorganisms which are to be transformed, may be used in this process.

In the first set of transformation experiments, the nifL gene is disrupted by insertional mutagenesis. An interposon of 2.0 kb having the 'first' antibiotic resistance marker gene (Kanamycin, Km+) is inserted in SalI restriction sites of the nifL gene of pCL6.2 construct, which is immediately upstream of the nifA gene and the construct is designated as pCL6.3 (FIG. 1C). This insertional mutagenesis renders the nifL gene non functional. The pCL6.3 recombinant plasmid is electroporated into the Azotobacter cells and homologous recombination is allowed to occur (FIG. 1E), wherein the integration of the interposon into the chromosome of the cell takes place via homologous recombination. Transformed cells that have undergone successful homologous recombination via two-point crossing over are detected by their resistance to the 'first' antibiotic marker (Km+), sensitivity to the 'second' antibiotic marker (Amp−) and their inability to fix atmospheric nitrogen (FIG. 1F).

In the second set of transformation experiments, 1.1 kb of DNA is deleted around the SalI sites from the pCL6.2 construct which renders partial deletion of the nifL gene and the 375 bp EcoRI-BamHI fragment containing the constitutive sigma-70' promoter/tet promoter of pBR322, as set forth in SEQ ID NO: 6, is inserted into SalI site to obtain the construct pCL6.4 (FIG. 1D). Other constitutive promoters, either synthetic or natural, but, compatible with the microorganism, that may be used are synthetic promoters and natural promoters like P1, nptII, CAT promoter etc. The recombinant construct pCL6.4 containing the constitutive heterologous promoter is further electroporated into the transformed *Azotobacter* cells obtained from the first set of transformation experiments. Successful homologous recombination via two-point crossing over between the flanking regions of the constitutive promoter and the chromosome of the first transformed *Azotobacter* cells result in deletion of the 'first' antibiotic resistance marker gene (Km), successful integration of the constitutive heterologous sigma-70/tet promoter operably linked to the nifA gene into the chromosome and the successful inhibition of the production of the Nif L protein of the microorganism (FIG. 1H). The recombinant *Azotobacter* obtained by this second transformation step comprises a non-functional nifL gene, an over-expressing nifA gene and is devoid of any antibiotic resistance (Km−). The recombinant *Azotobacter* obtained by this process are tested for successful transformation based on their sensitivity to the 'first' antibiotic (Km−) and their ability to fix atmospheric nitrogen. The partial deletion of the nifL gene and the insertion of the constitutive heterologous promoter upstream of the nifA gene are further confirmed by conventional methods available in the art. This recombinant *Azotobacter* has been designated as *Azotobacter chroococcum* HKD15 and has been submitted at the MTCC, IMTECH, India on 14 Dec. 2011. The Accession No. for the strain is MTCC 5679.

Figure 2:
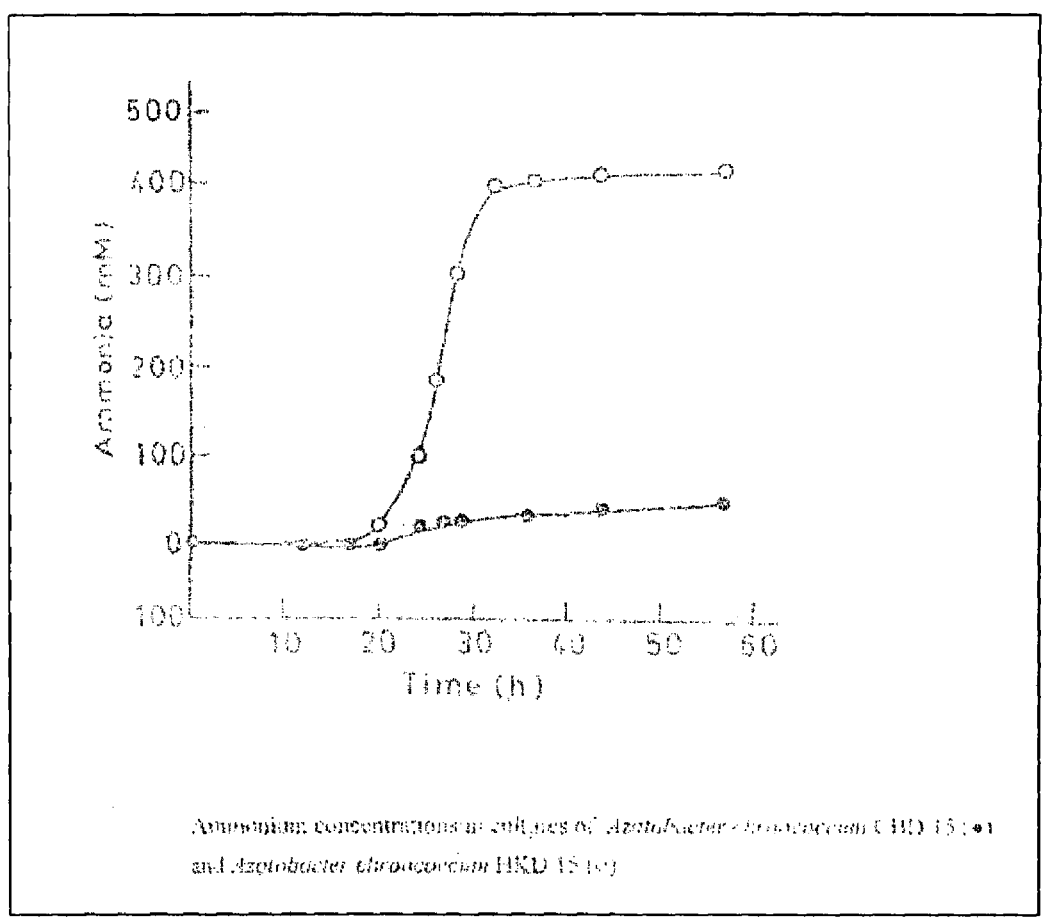
FIG. 2 shows the enhanced production and excretion of ammonia by *Azotobacter chroococcum* HKD15 compared to *Azotobacter chroococcum* CBD15.

The biological nitrogen fixation in the presence of fixed nitrogen by the recombinant microorganism, *Azotobacter chroococcum* HKD15 having Accession number MTCC 5679 is improved over that of the non-recombinant, native *Azotobacter chroococcum* CBD15. A 3-fold increase in nitrogen fixation was observed in the *Azotobacter chroococcum* HKD15 having Accession number MTCC 5679 compared to that of the non-recombinant native *Azotobacter chroococcum* CBD15 strain (Table 1). The *Azotobacter chroococcum* HKD15 having Accession number MTCC 5679 also show enhanced expression and excretion of ammonia wherein the ammonia excretion is increased by 9-fold compared to that of the non-recombinant native *Azotobacter chroococcum* CBD15 strain. Further, it was observed that expression is unaffected by the presence of fixed nitrogen in the form of urea or ammonium salts (FIG. 2). The biofertilizer efficacy of the recombinant microorganism, *Azotobacter chroococcum* HKD15 having Accession number MTCC 5679 was higher than the *Azotobacter chroococcum* CBD15, as observed when the crop plants were inoculated with the recombinant *Azotobacter chroococcum* HKD15 having Accession number MTCC 5679, compared to non-recombinant native *Azotobacter chroococcum* CBD15 strain (Table 2).

In one embodiment of the present invention, there is provided a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene.

In another embodiment of the present invention, there is provided a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene, wherein the microorganism is selected from a group consisting of Green sulfur bacteria, Firmibacteria, Thallobacteria, Heliobacteria, Cyanobacteria, *Campylobacter*, Proteobacteria, Archaeobacteria and Propionispira.

In another embodiment of the present invention, there is provided a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene, wherein the microorganism is *Azotobacter* spp.

In another embodiment of the present invention, there is provided a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene, wherein the *Azotobacter* is selected from a group consisting of *Azotobacter chroococcum*, *Azotobacter vinelandii*, *Azotobacter armenaicus*, *Azotobacter beijerinckii*, *Azotobacter nigricans* and *Azotobacter paspali*.

In a particular embodiment of the present invention, there is provided a recombinant *Azotobacter* having Accession number MTCC 5679 wherein, the *Azotobacter* is capable of fixing atmospheric nitrogen in presence of fixed nitrogen and oxygen and does not comprise antibiotic resistance marker gene.

In another embodiment of the present invention, there is provided a recombinant *Azotobacter* having Accession number MTCC 5679 wherein, the *Azotobacter* is capable of fixing atmospheric nitrogen in presence of fixed nitrogen and oxygen, wherein the *Azotobacter* comprises a disrupted chromosomal nifL gene and a chromosomal nifA gene operably linked to a heterologous constitutive promoter and does not comprise antibiotic resistance marker gene.

In another embodiment of the present invention, there is provided a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene, wherein the nifL gene is disrupted by insertional mutagenesis, deletion of genomic DNA, targeted gene disruption or introduction of a genomic or episomal vector.

In one embodiment of the present invention, there is provided a recombinant DNA molecule comprising a disrupted chromosomal nifL gene and a chromosomal nifA gene operably linked to a heterologous constitutive promoter.

In another embodiment of the present invention, there is provided a recombinant vector comprising the recombinant DNA molecule comprising a disrupted chromosomal nifL gene and a chromosomal nifA gene operably linked to a heterologous constitutive promoter.

In one embodiment of the invention, there is provided a process for producing a recombinant microorganism, wherein said process comprises (a) inserting a disrupted nifL gene and a nifA gene into the chromosome of a microorganism through homologous recombination with a recombinant DNA molecules comprising a disrupted chromosomal nifL gene, a nifA gene with native promoter and an antibiotic resistance marker gene to obtain a transformed microorganism, wherein the nifL gene is disrupted by insertional mutagenesis, deletion of genomic DNA, targeted gene disruption or introduction of a genomic or episomal vector and (b) inserting a heterologous constitutive promoter to the upstream of the nifA gene of the transformed microorganism through homologous recombination with a recombinant DNA molecule comprising a constitutive heterologous promoter to obtain a recombinant microorganism comprising a disrupted nifL gene and a nifA gene operably linked to the heterologous constitutive promoter, wherein the recombinant microorganism is capable of fixing atmospheric nitrogen in presence of fixed nitrogen and oxygen and does not comprise antibiotic resistance marker gene.

In one embodiment of the invention, there is provided a process for producing a recombinant microorganism, wherein said process comprises (a) inserting a disrupted nifL gene and a nifA gene into the chromosome of a microorganism through homologous recombination with a recombinant DNA molecule comprising a disrupted chromosomal nifL gene, a nifA gene with native promoter and an antibiotic resistance marker gene to obtain a transformed microorganism, wherein the nifL gene is disrupted by insertional mutagenesis carried out by interposon insertion and (b) inserting a heterologous constitutive promoter to the upstream of the nifA gene of the transformed microorganism through homologous recombination with recombinant DNA molecule comprising a constitutive heterologous promoter to obtain a recombinant microorganism comprising a disrupted nifL gene and a nifA gene operably linked to the heterologous constitutive promoter, wherein the recombinant microorganism is capable of fixing atmospheric nitrogen in presence of fixed nitrogen and oxygen and does not comprise antibiotic resistance marker gene.

In another embodiment of the invention there is provided a recombinant microorganism produced by the process comprising (a) inserting a disrupted nifL gene and a nifA gene into the chromosome of a microorganism through homologous recombination with a recombinant DNA molecules comprising a disrupted chromosomal nifL gene, a nifA gene with native promoter and an antibiotic resistance marker gene to obtain a transformed microorganism, wherein the nifL gene is disrupted by insertional mutagenesis, deletion of genomic DNA, targeted gene disruption or introduction of a genomic or episomal vector and (b) inserting a heterologous constitutive promoter to the upstream of the nifA gene of the transformed microorganism through homologous recombination with a recombinant DNA molecule comprising a constitutive heterologous promoter to obtain a recombinant microorganism comprising a disrupted nifL gene and a nifA gene operably linked to the heterologous constitutive promoter, wherein the recombinant microorganism is capable of fixing atmospheric nitrogen in presence of fixed nitrogen and oxygen and does not comprise antibiotic resistance marker gene.

In another embodiment of the invention there is provided a recombinant Azotobacter spp produced by the process comprising (a) inserting a disrupted nifL gene and a nifA gene into the chromosome of Azotobacter through homologous recombination with a recombinant DNA molecules comprising a disrupted chromosomal nifL, gene, a nifA gene with native promoter and an antibiotic resistance marker gene to obtain a transformed Azotobacter, wherein the nifL gene is disrupted by insertional mutagenesis, deletion of genomic DNA, targeted gene disruption or introduction of a genomic or episomal vector and (b) inserting a heterologous constitutive promoter to the upstream of the nifA gene of the transformed Azotobacter through homologous recombination with a recombinant DNA molecule comprising a constitutive heterologous promoter to obtain a recombinant Azotobacter comprising a disrupted nifL gene and a nifA gene operably linked to the heterologous constitutive promoter, wherein the recombinant Azotobacter is capable of fixing atmospheric nitrogen in presence of fixed nitrogen and oxygen and does not comprise antibiotic resistance marker gene.

In a particular embodiment of the present invention, there is provided a process for producing a recombinant Azotobacter, wherein said process comprises (a) providing a recombinant DNA construct comprising a disrupted nifL gene and a nifA gene with native promoter, wherein the nifL gene is disrupted by insertional mutagenesis, deletion of genomic DNA, targeted gene disruption or introduction of a genomic or episomal vector (b) inserting a disrupted nifL gene and a nifA gene with native promoter into the chromosome of a microorganism through homologous recombination by transforming an Azotobacter cell with the recombinant DNA construct of step a (c) selecting the transformed Azotobacter, wherein the transformed Azotobacter is unable to fix atmospheric nitrogen, (d) inserting a heterologous constitutive promoter to the upstream of the nifA gene of the in the transformed Azotobacter through homologous recombination with a recombinant DNA molecule comprising a constitutive heterologous promoter to obtain a recombinant Azotobacter comprising a. disrupted nifL gene and a nifA gene operably linked to the heterologous constitutive promoter and (e) selecting the recombinant Azotobacter from step (d) on nutrient medium lacking nitrogen source, wherein the recombinant Azotobacter is capable of fixing atmospheric nitrogen in presence of fixed nitrogen and oxygen and does not comprise antibiotic resistance marker gene.

In a particular embodiment of the present invention, there is provided a process for producing a recombinant Azotobacter, wherein said process comprises (a) providing a recombinant DNA construct comprising a disrupted nifL gene and a nifA gene with native promoter, wherein the nifL gene is disrupted by insertional mutagenesis carried out by interposon insertion (b) inserting a disrupted nifL gene and a nifA gene with native promoter into the chromosome of a microorganism through homologous recombination by transforming an Azotobacter cell with the recombinant DNA construct of step a (c) selecting the transformed Azotobacter, wherein the transformed Azotobacter is unable to fix atmospheric nitrogen, (d) inserting a heterologous constitutive promoter to the upstream of the nifA gene of the transformed Azotobacter through homologous recombination with a recombinant DNA molecule comprising a constitutive heterologous promoter to obtain a recombinant Azotobacter comprising a disrupted nifL gene and a nifA gene operably linked to the heterologous constitutive promoter and (e) selecting the recombinant Azotobacter from step (d) on nutrient medium lacking nitrogen source, wherein the recombinant Azotobacter is capable of fixing atmospheric nitrogen in presence of fixed nitrogen and oxygen and does not comprise antibiotic resistance marker gene.

In yet another embodiment of the invention, there is provided a process for producing a recombinant Azotobacter chroococcum HKD15 having Accession number MTCC 5679, wherein said process comprises (a) providing a recombinant DNA construct comprising a disrupted nifL gene and a nifA gene with native promoter, wherein the nifL gene is disrupted by insertional mutagenesis carried out by interposon insertion (b) inserting a disrupted nifL gene and a nifA gene with native promoter into the chromosome of a microorganism through homologous recombination by transforming an Azotobacter cell with the recombinant DNA construct of step a (c) selecting the transformed Azotobacter, wherein the transformed Azotobacter is unable to fix atmospheric nitrogen, (d) inserting a heterologous constitutive promoter to the upstream of the nifA gene of the transformed Azotobacter through homologous recombination with a recombinant DNA molecule comprising a constitutive heterologous promoter to obtain a recombinant *Azotobacter* comprising a disrupted nifL gene and a nifA gene operably linked to the heterologous constitutive promoter and (e) selecting the recombinant *Azotobacter* from step (d) on nutrient medium lacking nitrogen source, wherein the recombinant *Azotobacter* is capable of fixing atmospheric nitrogen in presence of fixed nitrogen and oxygen and does not comprise antibiotic resistance marker gene.

In another embodiment there is provided a recombinant *Azotobacter* produced by the process comprising (a) providing a recombinant DNA construct comprising a disrupted nifL gene and a nifA gene with native promoter, wherein the nifL gene is disrupted by insertional mutagenesis, deletion of genomic DNA, targeted gene disruption or introduction of a genomic or episomal vector (b) inserting a disrupted nifL gene and a nifA gene with native promoter into the chromosome of a microorganism through homologous recombination by transforming an *Azotobacter* cell with the recombinant DNA construct of step (a), (c) selecting the transformed *Azotobacter*, wherein the transformed *Azotobacter* is unable to fix atmospheric nitrogen, (d) inserting a heterologous constitutive promoter to the upstream of the nifA gene of the transformed *Azotobacter* through homologous recombination with a recombinant DNA molecule comprising a constitutive heterologous promoter to obtain a recombinant *Azotobacter* comprising a disrupted nifL gene and a nifA gene operably linked to the heterologous constitutive promoter and (e) selecting the recombinant *Azotobacter* from step (d) on nutrient medium lacking nitrogen source, wherein the recombinant *Azotobacter* is capable of fixing atmospheric nitrogen in presence of fixed nitrogen and oxygen and does not comprise antibiotic resistance marker gene.

In another embodiment there is provided a recombinant *Azotobacter* produced by the process comprising (a) providing a recombinant DNA construct comprising a disrupted nifL gene and a nifA gene with native promoter, wherein the nifL gene is disrupted by insertional mutagenesis carried out by interposon insertion (b) inserting a disrupted nifL gene and a nifA gene with native promoter into the chromosome of a microorganism through homologous recombination by transforming an *Azotobacter* cell with the recombinant DNA construct of step (a), (c) selecting the transformed *Azotobacter*, wherein the transformed *Azotobacter* is unable to fix atmospheric nitrogen, (d) inserting a heterologous constitutive promoter to the upstream of the nifA gene of the transformed *Azotobacter* through homologous recombination with a recombinant DNA molecule comprising a constitutive heterologous promoter to obtain a recombinant *Azotobacter* comprising a disrupted nifL gene and a nifA gene operably linked to the heterologous constitutive promoter and (e) selecting the recombinant *Azotobacter* from step (d) on nutrient medium lacking nitrogen source, wherein the recombinant *Azotobacter* is capable of fixing atmospheric nitrogen in presence of fixed nitrogen and oxygen and does not comprise antibiotic resistance marker gene.

In an advantageous embodiment of the present invention there is provided a composition comprising the recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene.

In another embodiment of the present invention there is provided a composition comprising a recombinant *Azotobacter* produced by the process comprising (a) providing a recombinant DNA construct comprising a disrupted nifL gene and a nifA gene with native promoter, wherein the nifL gene is disrupted by an interposon insertion (b) inserting a disrupted nifL gene and a nifA gene with native promoter into the chromosome of a microorganism through homologous recombination by transforming an *Azotobacter* cell with the recombinant DNA construct of step (a), (c) selecting the transformed *Azotobacter*, wherein the transformed *Azotobacter* is unable to fix atmospheric nitrogen, (d) inserting a heterologous constitutive promoter to the upstream of the nifA gene of the transformed *Azotobacter* through homologous recombination with a recombinant DNA molecule comprising a constitutive heterologous promoter to obtain a recombinant *Azotobacter* comprising a disrupted nifL gene and a nifA gene operably linked to the heterologous constitutive promoter and (e) selecting the recombinant *Azotobacter* from step (d) on nutrient medium lacking nitrogen source, wherein the recombinant *Azotobacter* is capable of fixing atmospheric nitrogen in presence of fixed nitrogen and oxygen and does not comprise antibiotic resistance marker gene.

In another embodiment of the present invention there is provided a composition comprising (a) a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene and (b) a carrier.

In another embodiment of the present invention there is provided a composition comprising (a) a recombinant *Azotobacter* comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene and (b) a carrier.

In another embodiment of the present invention there is provided a composition comprising (a) a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene and (b) an agriculturally acceptable carrier.

In a preferred embodiment of the present invention there is provided a biofertilizer composition comprising a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene.

In another embodiment of the present invention there is provided a biofertilizer composition comprising a recombinant *Azotobacter* comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene.

In another embodiment of the present invention there is provided a biofertilizer composition comprising a recombinant *Azotobacter* having Accession number MTCC 5679 comprising a disrupted chromosomal nifL gene and a chromosomal nifA gene operably linked to a heterologous constitutive promoter, wherein the *Azotobacter* is capable of fixing atmospheric nitrogen in presence of fixed nitrogen and oxygen and does not comprise antibiotic resistance marker gene.

In another embodiment of the present invention there is provided a composition comprising (a) a recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene and (b) one or more constituents selected from a group comprising sources of potassium, phosphorus, carbon, nitrogen, iron, sulphur, calcium, magnesium, zinc, trace elements, growth factors, pesticides, anti-termites, bacteria and/or algae.

In an embodiment of the present invention, there is provided use of a recombinant microorganism comprising a disrupted chromosomal nifL gene and a chromosomal nifA gene operably linked to a heterologous constitutive promoter for the preparation of a fertilizer composition for enhancing the fertility of the soil, wherein the microorganism is capable of fixing atmospheric nitrogen in presence of fixed nitrogen and oxygen and does not comprise antibiotic resistance marker gene.

In another embodiment of the present invention there is provided use of the recombinant *Azotobacter* comprising a disrupted chromosomal nifL gene and a chromosomal nifA gene operably linked to a heterologous constitutive promoter for the preparation of a fertilizer composition for enhancing the fertility of the soil, wherein the microorganism is capable of fixing atmospheric nitrogen in presence of fixed nitrogen and oxygen and does not comprise antibiotic resistance marker gene.

In another embodiment of the present invention there is provided use of the recombinant *Azotobacter* having Accession number MTCC 5679 comprising a disrupted chromosomal nifL gene and a chromosomal nifA gene operably linked to a heterologous constitutive promoter for the preparation of a fertilizer composition for enhancing the fertility of the soil, wherein the *Azotobacter* is capable of fixing atmospheric nitrogen in presence of fixed nitrogen and oxygen and does not comprise antibiotic resistance marker gene.

The present invention is not to be limited in scope by the specific embodiments described herein, which are intended for the purposes of exemplification only. Functionally-equivalent products, compositions, and methods are clearly within the scope of the invention, as described herein. Although the subject matter has been described in considerable detail with reference to certain preferred embodiments thereof, other embodiments are possible. As such, the spirit and scope of the appended claims should not be limited to the description of the preferred embodiment contained therein.

EXAMPLES

The disclosure will now be illustrated with working examples, which is intended to illustrate the working of disclosure and not intended to take restrictively to imply any limitations on the scope of the present disclosure.

The inventors initially carried out restriction deletion of a small part of the nifL gene of *Azotobacter vinelandii* UW, a strain obtained from the University of Wisconsin. A restriction fragment containing a constitutive sigma 70 promoter of 375 bases isolated from the plasmid pBR322 was inserted upstream of nifA of *Azotobacter vinelandii* UW. The expression of nifA, yield and excretion of ammonium was enhanced several fold, and this expression was unaffected by the presence of urea or ammonium salts.

Example 1

Isolation of nifL and nifA Genes of *Azotobacter chroococcum* CBD15

*Azotobacter chroococcum* CBD15, a strain isolated from the soil at Indian Agricultural Research Institute, Delhi, India, was used in the present study.

A genomic fragment of 7.5 kb size from the *Azotobacter chroococcum* CBD15 that contains the nifL gene comprising the nucleotide sequence as set forth in SEQ ID NO: 3 and the nifA genes was isolated using conventional methods and on the basis of homology with the known sequences of the nifL and the nifA genes of *Azotobacter vinelandii* UW. This fragment was purified and ligated into the cloning vector pUC7 at the BamHI restriction site to obtain a first recombinant vector. This recombinant vector comprising the 7.5 kb fragment was designated as pCL6 (FIG. 1A) and was introduced into competent *E. coli* cells. The transformed cells were screened using radiolabelled probes and colony hybridization technique.

The plasmid from these transformed cells harboring the 7.5 kb insert was further subjected to restriction digestion with various restriction enzymes. A fragment of 4.8 kb containing the nifL and nifA genes was obtained by restriction digestion with EcoRI restriction enzyme. The fragment was purified and subsequently cloned into the vector pUC7 to obtain a second recombinant vector. This recombinant vector comprising the 4.8 kb insert was designated as pCL6.2 (FIG. 1B) and used for further experiments.

Other known DNA sequences for nifL gene having GenBank Accession Numbers X70993.1 (SEQ ID NO: 1), SEQ ID NO: 3, NC_012560.1, X64832.1, 3. AF450501.1 can also be used for genetic manipulation and production of recombinant microorganism capable of fixing nitrogen in presence of fixed nitrogen, oxygen or a combination thereof.

Other known DNA sequences for nifA gene having GenBank Accession Numbers Y00554.1 (SEQ ID NO: 4), J03411.1 and M26751.1 can also be used for genetic manipulation and production of recombinant microorganism capable of fixing nitrogen in presence of fixed nitrogen, oxygen or a combination thereof.

Example 2

Site-Directed Insertional Mutagenesis of nifL

Insertion of the Interposon ΩKm into nifL of *Azotobacter chroococcum* CBD15

The 2.0 kb EcoRI fragment from pHP45 ΩKm (R. Fellay, J. Frey, H. Krisch, 1987; *Gene;* 52: 147) containing the interposon ΩKm was inserted into the pCL6.2 at the SalI sites of the nifL gene, which was immediately upstream of nifA. This construct is denoted as pCL6.3 and comprises the 'first' antibiotic resistance marker gene (Km+) (FIG. 1C). The ampicillin resistance marker gene of the plasmid is denoted as the 'second' antibiotic resistance marker gene (Amp+).

Electroporation of *Azotobacter chroococcum* CBD15 with pCL6.3 for Insertion of the Interposon ΩKm at the nifL Gene in its Genome

*Azotobacter chroococcum* CBD15 was electroporated with the recombinant plasmid construct pCL6.3 to obtain the first set of transformed cells. The transformed cells showing kanamycin resistance (Km+) were selected. The cells were assayed for absence of ampicillin resistance (Amp–) and absence of nitrogen fixation. This ensured that pCL6.3 was not stable in *Azotobacter chroococcum* CBD15 and the kanamycin resistance of the cells was the result of homologous recombination via two point cross-over between the flanking regions of the interposon ΩKm in pCL6.3 and the chromosome of *Azotobacter chroococcum* CBD15 (FIGS. 1E and 1F).

Example 3

Partial Deletion of NifL Gene and Cloning of the pBR322 Constitutive Promoter

The 375 bp EcoRI-BamHI fragment from pBR322 comprising the constitutive promoter (nucleotides 1 to 377), as set forth in SEQ ID NO: 6, was used.

A 1.1 kb DNA fragment around the Sal I sites of pCL6.2 was deleted and the EcoRI-BamHI fragment of 375 bp containing the pBR322 constitutive promoter (SEQ ID NO: 6) was inserted at the site of deletion of 1.1 kb DNA fragment around the SalI sites in pCL6.2. This construct containing the constitutive promoter was denoted as pCL6.4 (FIG. 1D).

Example 4

Integration of Partially Deleted NifL and the Constitutive Promoter Upstream of nifA into the Genome of the Microorganism The first set of transformed *Azotobacter chroococcum* CBD15 cells comprising the ΩKm interposon and the 'first' antibiotic resistance marker gene (Km+) were electroporated with the recombinant plasmid construct pCL6.4 (FIG. 1G). Those cells that were successfully transformed by the result of homologous recombination via two point cross-over between the flanking regions of the pBR322 constitutive promoter in pCL6.4 and the chromosome of the first set of transformed cells of *Azotobacter chroococcum* CBD15 (Km+) were assayed for absence of 'first' antibiotic resistance marker gene and their ability to fix nitrogen (FIG. 1H). The transformed cells that have undergone successful homologous recombination are sensitive to the 'first' antibiotic resistance marker gene, kanamycin. The recombinant microorganism has been designated as *Azotobacter chroococcum* HKD15. The recombinant microorganism has been submitted at the MTCC, IMTECH, India on 14 Dec. 2011. The Accession No. for the strain is MTCC 5679.

The deletion of a part of the nifL gene and the insertion of the pBR322 constitutive promoter in the chromosome of *Azotobacter chroococcum* HKD15 has been confirmed by Southern blotting and PCR analysis.

Example 5

Characterization of the Recombinant *Azotobacter chroococcum* HKD15

Nitrogen Fixation Activity of *Azotobacter chroococcum* HKD15 in the Presence of Fixed Nitrogen It is difficult to assay reduction of nitrogen. It is, however, known that the enzyme nitrogenase is also capable of reducing acetylene. Hence, the reduction of acetylene to ethylene is accepted as a measure of nitrogenase. The bacterial culture in a screw-capped tube is fed with specific amount of gaseous acetylene and incubated at 30° C. After 24 hours, the amount of ethylene produced along with the amount of acetylene left over are monitored by gas chromatography and compared with the initial amount of acetylene.

Acetylene reduction was enhanced 3-fold by the constitutive promoter in *Azotobacter chroococcum* HKD15 compared to the native strain *Azotobacter chroococcum* CBD15 (see Table 1).

TABLE 1

Effect of fixed nitrogen source (ammonium acetate) on acetylene reduction by *Azotobacter chroococcum* CBD 15 and *Azotobacter chroococcum* HKD 15

| Sl No. | Strain | Nitrogen status | Percent acetylene reduced |
|---|---|---|---|
| 1. | CBD 15 | N minus | 14.2 ± 2.4 |
| 2. | CBD 15 | N plus (10 mM) | 1.9 ± 0.7 |
| 3. | CBD 15 | N plus (20 mM) | 1.7 ± 0.5 |
| 4. | HKD 15 | N minus | 42.9 ± 2.5 |
| 5. | HKD 15 | N plus (10 mM) | 41.1 ± 1.9 |
| 6. | HKD 15 | N plus (20 mM) | 39.6 ± 1.6 |

Ammonia Production and Excretion by *Azotobacter chroococcum* HKD15

Samples of cultures growing at 30° C. were withdrawn periodically, centrifuged and ammonium in the supernatant solution was estimated according to the indophenol method [Bergersen F. J, 1980, Methods for evaluating biological nitrogen fixation. John Wiley and Sons]. This consisted of the addition of 0.5 ml of phenol-sodium nitroprusside solution (phenol, 50 g/liter; sodium nitroprusside, 0.25 g/liter), 0.5 ml of sodium hypochlorite solution (0.1 M), and 2 ml of distilled water. The mixture was incubated for 30 min at room temperature. The optical density of the solution was then read at $A_{625}$ and the ammonium concentration was estimated from a standard curve obtained with ammonium solutions at various concentrations assayed with the same reagent solutions.

It was found that the recombinant microorganism *Azotobacter chroococcum* CBD15 showed a 9-fold increase in ammonia excretion compared with *Azotobacter chroococcum* HKD15. FIG. 2 shows the ammonia excretion by the recombinant and the non-recombinant *Azotobacter* microorganism.

Effect of *Azotobacter chroococcum* HKD15 as Plant Inoculants

Wheat seeds are soaked in a suspension of the recombinant or the non-recombinant microorganism for three hours and air dried at around 25° C. for 12-24 hours. The treated seeds are then sown in pots of 30 cm diameter. Three plants are kept per pot. The seeds were sown in mid-November and the crop was harvested in mid-April.

The yield of the crop in the absence of chemical fertilizer and the presence of the recombinant microorganism HKD15 was found to be higher than the yield of the crop in the presence of *Azotobacter chroococcum* CBD15, as shown in Table 2. The recombinant *Azotobacter chroococcum* HKD15 was found to be an efficacious crop inoculant and a biofertilizer.

TABLE 2

Effect of inoculation of wheat seed with *Azotobacter chroococcum* on yield of wheat crop in pot experiments

| Sl. No. | Treatment | Crop yield per 100 plants |
|---|---|---|
| 1. | Absence of urea, Absence of inoculation with *Azotobacter* spp. | 155 gm |

TABLE 2-continued

Effect of inoculation of wheat seed with *Azotobacter chroococcum* on yield of wheat crop in pot experiments

| Sl. No. | Treatment | Crop yield per 100 plants |
|---|---|---|
| 2. | Absence of urea Inoculation with *Azotobacter chroococcum* CBD15 | 167 gm |
| 3. | Absence of urea Inoculation with *Azotobacter chroococcum* HKD15 | 246 gm |

SEQ ID NO: 1 shows nucleotide sequence of the nifL gene from *Azotobacter vinelandii* (1927 bp) (GENBANK: X70993.1)

```
TGCCAGCGCT CAAAATTTGC ACAGGCGTAT CGCGGGAGCC
CCTCTAAAAT TGACCTGGAT CAACAAATAG CTTCGGCACG
CCAGCCGCCT ATCCACCCGG CGGCCCCGGT TTTGTAAGGT
TTGTGACAGC TCGTTACTGA GCCTGCCGCC CGGCTGTGCG
CTTTCGCACA GCTAGAGGGC GACCACCCCG AAAATCCATG
TTTCGAGGTT TTTCCGAGCA ATTCGGCGCA CCCGGGCGAT
TAAGGTGCGG CACAGGATTT GCTAATCTTC TCTCAGGCCC
AACACGCCCC TCCGGCGGAC GCAGCCGCGC TCGCCGGTTT
TCTTGGATAG ACGAGGCACA GCATGACCCC GGCCAACCCG
ACCCTGAGCA ACGAGCCGCA AGCGCCTCAC GCCGAGAGCG
ACGAGCTGCT TCCCGAGATC TTTCGCCAGA CGGTGGAGCA
TGCGCCCATC GCCATTTCCA TCACCGACCT CAAGGCCAAC
ATTCTTTACG CCAATCGCGC TTTCCGCACC ATCACCGGCT
ACGGCAGCGA GGAAGTGCTC GGCAAGAACG AATCGATCCT
CTCCAACGGC ACCACGCCGC GCCTGGTCTA CCAGGCCCTG
TGGGGCCGGC TGGCGCAGAA GAAGCCCTGG TCCGGCGTGC
TGGTCAACCG CCGCAAGGAC AAGACCCTGT ACCTGGCCGA
ACTGACCGTG GCGCCGGTGC TCAACGAGGC CGGCGAGACC
ATCTACTACC TGGGCATGCA CCGCGACACC AGCGAATTGC
ACGAACTGGA ACAACGCGTC AACAACCAGC GCCTGATGAT
CGAGGCGGTG GTCAACGCCG CCCCGGCGGC GATGGTGGTG
CTCGACCGCC AGCACCGGGT GATGCTCTCC AACCCGAGCT
TCTGCCGCCT GGCCCGCGAC CTGGTCGAGG ATGGCAGCAG
CGAGAGCCTG GTGGCGCTGC TGCGGGAAAA CCTCGCCGCC
CCCTTCGAGA CGCTGGAAAA CCAGGGCAGC GCCTTCTCCG
GCAAGGAGAT CTCCTTCGAC CTGGGCGGCC GCTCGCCGCG
CTGGCTGTCC TGCCACGGCC GGGCCATCCA CATCGAGAAC
GAGCAGGCCC ACGTGTTCTT CGCGCCCACC GAGGAACGCT
ACCTGCTGCT GACCATCAAC GACATCTCCG AGCTGCGCCA
GAAGCAGCAG GATTCGCGGC TCAACGCGCT GAAGGCGCTG
ATGGCCGAGG AAGAGCTGCT GCAAGGCATG CGCGAGACCT
TCAACGCCGC CATCCATCGC CTGCAGGGCC CGGTCAACCT
GATCAGCGCG GCGATGCGCA TGCTCGAACG GCGCCTCGGC
GACAAGGCCG GCAACGACCC GGTGCTGAGC GCCATGCGCG
AAGCCAGCAC GGCCGGAATG GAGGCACTGG AGAACCTCAG
TGGCTCCATT CCGGTGCGCA TGGCCGAGTC CAAGATGCCG
GTCAACCTCA ACCAGTTGAT CCGCGAGGTG ATCACCCTGT
GCACCGACCA GTTGCTGGCC CAGGGCATCG TCGTCGACTG
GCAGCCGGCG CTGCGCCTGC CCTGGGTGAT GGGCGGGGAA
AGCAGCCTGC GCAGCATGAT CAAGCACCTG GTCGACAACG
CCATCGAGTC CATGAGCCAG AACCAGGTCA GCCGCCGCGA
GCTGTTCATC AGCACCCGCG TGGAGAACCA CCTGGTGCGC
ATGGAGATCA CCGACAGCGG CCCGGGCATT CCGCCCGACC
TGGTGCTGAA GGTGTTCGAG CCGTTCTTCA GCACCAAGCC
GCCACACCGC GTCGGGCGCG GCATGGGCCT GCCGGTGGTG
CAGGAGATCG TCGCCAAGCA CGCCGGCATG GTGCACGTAG
ACACCGACTA TCGCGAAGGC TGCCGGATCG TCGTCGAGCT
GCCCTTCTCG GCCTCCACCT GAACAGCGAC AGGGAATGCC
CATGAAT
```

SEQ ID NO: 2 shows amino acid sequence encoded by the SEQ ID NO: 1

```
MTPANPTLSNEPQAPHAESDELLPEIFRQTVEHAPIAISITDLKANILYA
NRAFRTITGYGSEEVLGKNESILSNGTTPRLVYQALWGRLAQKKPWSGVL
VNRRKDKTLYLAELTVAPVLNEAGETIYYLGMHRDTSELHELEQRVNNQR
LMIEAVVNAAPAAMVVLDRQHRVMLSNPSFCRLARDLVEDGSSESLVALL
RENLAAPFETLENQGSAFSGKEISFDLGGRSPRWLSCHGRAIHIENEQAH
VFFAPTEERYLLLTINDISELRQKQQDSRLNALKALMAEEELLQGMRETF
NAAIHRLQGPVNLISAAMRMLERRLGDKAGNDPVLSAMREASTAGMEALE
NLSGSIPVRMAESKMPVNLNQLIREVITLCTDQLLAQGIVVDWQPALRLP
WVMGGESSLRSMIKHLVDNAIESMSQNQVSRRELFISTRVENHLVRMEIT
DSGPGIPPDLVLKVFEPFFSTKPPHRVGRGMGLPVVQEIVAKHAGMVHVD
TDYREGCRIVVELPFSAST
```

SEQ ID NO: 3 shows Partial nucleotide sequence of nifL gene of *Azotobacter chroococcum* CBD15 (1.4 kb)

```
ATCGCGCTTTCCGCACCATCACCGGCTACGGCAGCGAGGAAGTGCTCGGC
AAGAACGAATCGATCCTCTCCAACGGCACCACGCCGCGCCTGGTCTACCA
GGCCCTGTGGGGCTGGCTGGCGCAGAAGAAGCCCTGGTCCGGCGTGCTGG
TCAACCGCCGCAAGGACAAGACCCTGTACCTGGCCGAACTGACCGTGGCG
CCGGTGCTCAACGAGGCCGGCGAGACCATCTACTACCTGGGCATGCACCG
CGACACCAGCGAATTGCACGAACTGGAACAACGCGTCAACAACCAGCGCC
TGATGATCGAGGCGGTGGTCAGCGCCGCCCCGGCGGCGATGGTGGTGCTC
```

```
GACCGCCAGCACCGGGTGATGCTCTCCAACCCGAGCTTCTGCCGCCTGGC
CCGCGACCTGGTCGAGGATGGCAGCAGCGAGAGCCTGGTGGCGCTGCTGC
GGGAAAACCTCGCCGCCCCCTTCGAGACGCTGGAAAACCAGGGCAGCGCC
TTCTCCGGCAAGGAGATCTCCTTCGACCTGGGCGGCCGCTCGCCGCGCTG
GCTGTCCTGCCACGGCCGGGCCATCCACATCGAGAACGAGCAGGCCCACG
TGTTCTTCGCGCCCACCGAGGAACGCTACCCTGCTGCTGACCATCAACGA
CATCTCCGAGCTGCGCCAGAAGCAGCAGGATTCGCGGCTCAACGCGCTGA
AGGCGCTGATGGCCGAGGAAGAGCTGCTGGAAGGCATGCGCGAGACCTTC
AACGCCGCCATCCATCGCCTGCAGGGCCCGGCCAACCTGATCAGCGCGGC
GATGCGCATGCTCGAACGGCGCCTCGGCGGCAAGGCCGGCAACGACCCGG
TGCTGAGCGCCATGCGCGAAGCCAGCACGGCCGGAATGGAGGCACTGGAG
AACCTCAGTGGCTCCATTCCGGTGCGCATGGCCGAGTCCAAGATGCCGGT
CAACCTCAACCAGTTGATCCGCGAGGTGATCACCCTGTGCACCGACCAGT
TGCTGGCCCAGGGCATCGTCGTCGACTGGCAGCCGGCGCTGCGCCTGCCC
TGGGTGATGGGCGGGAAAGCAGCCTGCGCAGCATGATCAAGCACCTGGT
CGACAACGCCATCGAGTCCATGAGCCAGAACCAGGTCAGCCGCCGCGAGC
TGTTCATCAGCACCCGCGTGGAGAACCACCTGGTGCGCATGGAGATCACC
GACAGCGGCCCGGGCATTCCGCCCGACCTGGTGCTGAAGGTGTTCGAGCC
GTTCTTCAGCACCAAGCCGCCACACCGCGTCGGGCGCGGCACGGGCCTGC
CGGTGGTGCAGGAGATCGTCGCCAAGCACGCCGGCATGGTGCACGTAGAC
ACCGACTATCGCGAAGGCTGCCGGATCGTCGTCGAGCTGCCCTTCTCGGC
CTCACCTCTAGAGTCGA
```

SEQ ID NO: 4 shows nucleotide sequence of nifA gene. of *Azotobacter vinelandii* (1569 bp) (GenBank: Y00554.1)

```
ATGAATGCA ACCATCCCTC AGCGCTCGGC CAAACAGAAC
CCGGTCGAAC TCTATGACCT GCAATTGCAG GCCCTGGCGA
GCATCGCCCG CACGCTCAGC CGCGAACAAC AGATCGACGA
ACTGCTCGAA CAGGTCCTGG CCGTACTGCA CAATGACCTC
GGCCTGCTGC ATGGCCTGGT GACCATTTCC GACCCGGAAC
ACGGCGCCCT GCAGATCGGC GCCATCCACA CCGACTCGGA
AGCGGTGGCC CAGGCCTGCG AAGGCGTGCG CTACAGAAGC
GGCGAAGGCG TGATCGGCAA CGTGCTCAAG CACGGCAACA
GCGTGGTGCT CGGGCGCATC TCCGCCGACC CGCGCTTTCT
CGACCGCCTG GCGCTGTACG ACCTGGAAAT GCCGTTCATC
GCCGTGCCGA TCAAGAACCC CGAGGGCAAC ACCATCGGCG
TGCTGGCGGC CCAGCCGGAC TGCCGCGCCG ACGAGCACAT
GCCCGCGCGC ACGCGCTTCC TGGAGATCGT CGCCAACCTG
CTGGCGCAGA CCGTGCGCCT GGTGGTGAAC ATCGAGGACG
GCCGCGAGGC GGCCGACGAG CGCGACGAAC TGCGTCGCGA
GGTGCGCGGC AAGTACGGCT TCGAGAACAT GGTGGTGGGC
CACACCCCCA CCATGCGCCG GGTGTTCGAT CAGATCCGCC
GGGTCGCCAA GTGGAACAGC ACCGTACTGG TCCTCGGCGA
GTCCGGTACC GGCAAGGAAC TGATCGCCAG CGCCATCCAC
TACAAGTCGC CGCGCGCGCA CCGCCCCTTC GTCCGCCTGA
ACTGCGCCGC GCTGCCGGAA ACCCTGCTCG AGTCCGAACT
CTTCGGCCAC GAGAAGGGCG CCTTCACCGG CGCGGTGAAG
CAGCGCAAGG GGCGTTTCGA GCAGGCCGAC GGCGGCACCC
TGTTCCTCGA CGAGATCGGC GAGATCTCGC CGATGTTCCA
GGCCAAGCTG CTGCGCGTGC TGCAGGAAGG CGAGTTCGAG
CGGGTCGGCG GCAACCAGAC GGTGCGGGTC AACGTGCGCA
TCGTCGCCGC CACCAACCGC GACCTGGAAA GCGAGGTGGA
AAAGGGCAAG TTCCGCGAGG ACCTCTACTACCGCCTGAAC
GTCATGGCCA TCCGCATTCC GCCGCTGCGC GAGCGTACCG
CCGACATTCCCGAACTGGCG GAATTCCTGC TCGGCAAGAT
CGGCCGCCAG CAGGGCCGCC CGCTGACCGT CACCGACAGC
GCCATCCGCC TGCTGATGAG CCACCGCTGG CCGGGCAACG
TGCGCGAACT GGAGAACTGC CTGGAGCGCT CGGCGATCAT
GAGCGAGGAC GGCACCATCA CCCGCGACGT GGTCTCGCTG
ACCGGGGTCGACAACGAGAG CCCGCCGCTC GCCGCGCCGC
TGCCCGAGGT CAACCTGGCC GACGAGACCC TGGACGACCG
CGAACGGGTG
ATCGCCGCCCTCGAACAGGCCGGCTGGGTGCAGGCCAAGGCCGCGCGGC
TGCTGGGCATGACGCCGCGGCAGATCGCCTACCGCATCCAGACCCTCAA
CATCCACATGCGCAAGATCTGA
```

SEQ ID NO: 5 shows amino acid sequence of the product encoded by SEQ ID NO: 4

```
MNATIPQRSAKQNPVELYDLQLQALASIARTLSREQQIDELLEQVLAVLH
NDLGLLHGLVTISDPEHGALQIGAIHTDSEAVAQACEGVRYRSGEGVIGN
VLKHGNSVVLGRISADPRFLDRLALYDLEMPFIAVPIKNPEGNTIGVLAA
QPDCRADEHMPARTRFLEIVANLLAQTVRLVVNIEDGREAADERDELRRE
VRGKYGFENMVVGHTPTMRRVFDQIRRVAKWNSTVLVLGESGTGKELIAS
AIHYKSPRAHRPFVRLNCAALPETLLESELFGHEKGAFTGAVKQRKGRFE
QADGGTLFLDEIGEISPMFQAKLLRVLQEGEFERVGGNQTVRVNVRIVAA
TNRDLESEVEKGKFREDLYYRLNVMAIRIPPLRERTADIPELAEFLLGKI
GRQQGRPLTVTDSAIRLLMSHRWPGNVRELENCLERSAIMSEDGTITRDV
VSLTGVDNESPPLAAPLPEVNLADETLDDRERVIAALEQAGWVQAKAARL
LGMTPRQIAYRIQTLNIHMRKI
```

SEQ ID NO: 6 shows nucleotide sequence of the fragment of DNA from the plasmid pBR322 inserted upstream of the nif A gene of *Azotobacter*

GAATTCTCAT GTTTGACAGC TTATCATCGA TTAGCTTTAA

TGCGGTAGTT TATCACAGTT AAATTGCTAA CGCAGTCAGG

CACCGTGTAT GAAATCTAAC AATGCGCTCA TCGTCATCCT

CGGCACCGTC ACCCTGGATG CTGTAGGCAT AGGCTTGGTT

ATGCCGGTAC TGCCGGGCCT CTTGCGGGAT ATCGTCCATT

-continued

CCGACAGCAT CGCCAGTCAC TATGGCGTGC TGCTAGCGCT

ATATGCGTTG ATGCAATTTC TATGCGCACC CGTTCTCGGA

GCACTGTCCG ACCGCTTTGG CCGCCGCCCA GTDCCTGCTC

GCTTCGCTAC TTGGAGCCAC TATCACTACG CGATCATGGC

GACCACACCC GTCCTGTGGA TCC

---

The invention claimed is:

1. A recombinant microorganism comprising a disrupted chromosomal nifL gene and a chromosomal nifA gene operably linked to a heterologous constitutive promoter, wherein the microorganism is capable of fixing atmospheric nitrogen in presence of fixed nitrogen and oxygen and does not comprise antibiotic resistance marker gene.

2. The recombinant microorganism as claimed in claim 1, wherein the microorganism is selected from a group consisting of Green sulfur bacteria, Firmibacteria, Thallobacteria, Heliobacteria, Cyanobacteria, *Campylobacter*, Proteobacteria, Archaeobacteria and Propionispira.

3. The recombinant microorganism as claimed in claim 1, wherein the microorganism is *Azotobacter* spp.

4. The recombinant microorganism as claimed in claim 3, wherein the *Azotobacter* is selected from a group consisting of *Azotobacter chroococcum, Azotobacter vinelandii, Azotobacter armenaicus, Azotobacter beijerinckii, Azotobacter nigricans* and *Azotobacter paspali*.

5. A recombinant *Azotobacter* having Accession number MTCC 5679, wherein the *Azotobacter* is capable of fixing atmospheric nitrogen in presence of fixed nitrogen and oxygen and does not comprise antibiotic resistance marker gene.

6. The recombinant microorganism as claimed in claim 1, wherein the nifL gene is disrupted by insertional mutagenesis, deletion of genomic DNA, targeted gene disruption or introduction of a genomic or episomal vector.

7. A recombinant DNA molecule comprising a disrupted chromosomal nifL gene and a chromosomal nifA gene operably linked to a heterologous constitutive promoter.

8. A recombinant vector comprising the recombinant DNA molecule as claimed in claim 7.

9. A composition comprising the recombinant microorganism as claimed in claim 1.

10. The composition as claimed in claim 9, wherein the composition optionally comprises a carrier.

11. The composition as claimed in claim 10, wherein the carrier is an agriculturally acceptable carrier.

12. The composition as claimed in claim 9, wherein the composition is a biofertilizer.

13. The composition as claimed in claim 9, optionally comprising one or more constituents selected from a group comprising sources of potassium, phosphorus, carbon, nitrogen, iron, sulphur, calcium, magnesium, zinc, trace elements, growth factors, pesticides, anti-termites, bacteria, algae.

14. A process for producing a recombinant microorganism, as claimed in claim 1, said process comprising:
    (a) disrupting a chromosomal nifL gene comprising insertion of antibiotic resistance marker gene into said chromosomal nifL gene;

(b) inserting said disrupted nifL gene and a chromosomal nifA gene into a chromosome of a microorganism, wherein said disrupted nifL gene is upstream of said chromosomal nifA gene;
(c) replacing said antibiotic resistance marker gene with a heterologous constitutive promoter operably linked to said nifA gene.

15. The process as claimed in claim 14, wherein said insertion of antibiotic resistance marker gene is carried out by interposon.

16. Method for enhancing fertility of a soil comprising: preparing a fertilizer composition comprising the recombinant microorganism as claimed in claim 1; and
providing said fertilizer composition to said soil.

* * * * *

SEQUENCE LISTING

<160> NUMBER OF SEQ ID NOS: 6

<210> SEQ ID NO 1
<211> LENGTH: 1927
<212> TYPE: DNA
<213> ORGANISM: Azotobacter vinelandii

<400> SEQUENCE: 1

| | | | | | |
|---|---|---|---|---|---|
| tgccagcgct | caaaatttgc | acaggcgtat | cgcgggagcc | cctctaaaat | tgacctggat | 60 |
| caacaaatag | cttcggcacg | ccagccgcct | atccacccgg | cggccccggt | tttgtaaggt | 120 |
| ttgtgacagc | tcgttactga | gcctgccgcc | cggctgtgcg | ctttcgcaca | gctagagggc | 180 |
| gaccaccccg | aaaatccatg | tttcgaggtt | tttccgagca | attcggcgca | cccgggcgat | 240 |
| taaggtgcgg | cacaggattt | gctaatcttc | tctcaggccc | aacacgcccc | tccggcggac | 300 |
| gcagccgcgc | tcgccggttt | tcttggatag | acgaggcaca | gcatgacccc | ggccaacccg | 360 |
| accctgagca | acgagccgca | agcgcctcac | gccgagagcg | acgagctgct | tcccgagatc | 420 |
| tttcgccaga | cggtggagca | tgcgcccatc | gccatttcca | tcaccgacct | caaggccaac | 480 |
| attctttacg | ccaatcgcgc | tttcgcgcacc | atcaccggct | acggcagcga | ggaagtgctc | 540 |
| ggcaagaacg | aatcgatcct | ctccaacggc | accacgccgc | gcctggtcta | ccaggccctg | 600 |
| tggggccggc | tggcgcagaa | gaagcccctgg | tccggcgtgc | tggtcaaccg | ccgcaaggac | 660 |
| aagaccctgt | acctggccga | actgaccgtg | gcgccggtgc | tcaacgaggc | cggcgagacc | 720 |
| atctactacc | tgggcatgca | ccgcgacacc | agcgaattgc | acgaactgga | acaacgcgtc | 780 |
| aacaaccagc | gcctgatgat | cgaggcggtg | gtcaacgccg | ccccggcggc | gatggtggtg | 840 |
| ctcgaccgcc | agcaccgggt | gatgctctcc | aacccgagct | tctgccgcct | ggcccgcgac | 900 |
| ctggtcgagg | atggcagcag | cgagagcctg | gtggcgctgc | tgcgggaaaa | cctcgccgcc | 960 |
| cccttcgaga | cgctggaaaa | ccagggcagc | gccttctccg | gcaaggagat | ctccttcgac | 1020 |
| ctgggcggcc | gctcgccgcg | ctggctgtcc | tgccacggcc | gggccatcca | catcgagaac | 1080 |
| gagcaggccc | acgtgttctt | cgcgcccacc | gaggaacgct | acctgctgct | gaccatcaac | 1140 |
| gacatctccg | agctgcgcca | gaagcagcag | gattcgcggc | tcaacgcgct | gaaggcgctg | 1200 |
| atggccgagg | aagagctgct | gcaaggcatg | cgcgagacct | tcaacgccgc | catccatcgc | 1260 |
| ctgcagggcc | cggtcaacct | gatcagcgcg | gcgatgcgca | tgctcgaacg | gcgcctcggc | 1320 |
| gacaaggccg | gcaacgaccc | ggtgctgagc | gccatgcgcg | aagccagcac | ggccggaatg | 1380 |
| gaggcactgg | agaacctcag | tggctccatt | ccggtgcgca | tggccgagtc | caagatgccg | 1440 |
| gtcaacctca | accagttgat | ccgcgaggtg | atcaccctgt | gcaccgacca | gttgctggcc | 1500 |
| cagggcatcg | tcgtcgactg | gcagccggcg | ctgcgcctgc | cctgggtgat | gggcggggaa | 1560 |
| agcagcctgc | gcagcatgat | caagcacctg | gtcgacaacg | ccatcgagtc | catgagccag | 1620 |
| aaccaggtca | gccgccgcga | gctgttcatc | agcacccgcg | tggagaacca | cctggtgcgc | 1680 |

```
atggagatca ccgacagcgg cccgggcatt ccgcccgacc tggtgctgaa ggtgttcgag    1740
ccgttcttca gcaccaagcc gccacaccgc gtcgggcgcg catgggcct gccggtggtg     1800 caggagatcg tcgccaagca cgccggcatg gtgcacgtag acaccgacta tcgcgaaggc    1860
tgccggatcg tcgtcgagct gcccttctcg gcctccacct gaacagcgac agggaatgcc    1920
catgaat                                                              1927
```

<210> SEQ ID NO 2
<211> LENGTH: 513
<212> TYPE: PRT
<213> ORGANISM: Azotobacter vinelandii

<400> SEQUENCE: 2

```
Met Thr Pro Ala Asn Pro Thr Leu Ser Asn Glu Pro Gln Ala Pro His
1               5                   10                  15

Ala Glu Ser Asp Glu Leu Leu Pro Glu Ile Phe Arg Gln Thr Val Glu
            20                  25                  30

His Ala Pro Ile Ala Ile Ser Ile Thr Asp Leu Lys Ala Asn Ile Leu
        35                  40                  45

Tyr Ala Asn Arg Ala Phe Arg Thr Ile Thr Gly Tyr Gly Ser Glu Glu
    50                  55                  60

Val Leu Gly Asn Glu Ser Ile Leu Ser Asn Gly Thr Thr Pro Arg Leu
65                  70                  75                  80

Val Tyr Gln Ala Leu Trp Gly Arg Leu Ala Gln Lys Pro Trp Ser Gly
                85                  90                  95

Val Leu Val Asn Arg Arg Lys Asp Lys Thr Leu Tyr Leu Ala Glu Leu
            100                 105                 110

Thr Val Ala Pro Val Leu Asn Glu Ala Gly Glu Thr Ile Tyr Tyr Leu
        115                 120                 125

Gly Met His Arg Asp Thr Ser Glu Leu His Glu Leu Glu Gln Arg Val
    130                 135                 140

Asn Asn Gln Arg Leu Met Ile Glu Ala Val Val Ala Ala Pro Ala Ala
145                 150                 155                 160

Met Val Val Leu Asp Arg Gln His Arg Val Met Leu Ser Asn Pro Ser
                165                 170                 175

Phe Cys Arg Leu Ala Arg Asp Leu Val Glu Asp Gly Ser Ser Glu Ser
            180                 185                 190

Leu Val Ala Leu Leu Arg Glu Asn Leu Ala Ala Pro Phe Glu Thr Leu
        195                 200                 205

Glu Asn Gln Gly Ser Ala Phe Ser Gly Lys Glu Ile Ser Phe Asp Leu
    210                 215                 220

Gly Gly Arg Ser Pro Arg Trp Leu Ser Cys His Gly Arg Ala Ile His
225                 230                 235                 240

Ile Glu Asn Glu Gln Ala His Val Phe Phe Ala Pro Thr Glu Glu Arg
                245                 250                 255

Tyr Leu Leu Leu Thr Ile Asn Asp Ile Ser Glu Leu Arg Gln Lys Gln
            260                 265                 270

Gln Asp Ser Arg Leu Asn Ala Leu Lys Ala Leu Met Ala Glu Glu Glu
        275                 280                 285

Leu Leu Gln Gly Met Arg Glu Thr Phe Asn Ala Ala Ile His Arg Leu
    290                 295                 300

Gln Gly Pro Val Asn Leu Ile Ser Ala Ala Met Arg Met Leu Glu Arg
305                 310                 315                 320
```

```
Arg Leu Gly Asp Ala Gly Asn Asp Pro Val Leu Ser Ala Met Arg Glu
            325                 330                 335
Ala Ser Thr Ala Gly Met Glu Ala Leu Glu Asn Leu Ser Gly Ser Ile
        340                 345                 350
Pro Val Arg Met Ala Glu Ser Met Pro Val Asn Leu Asn Gln Leu Ile
    355                 360                 365
Arg Glu Val Ile Thr Leu Cys Thr Asp Gln Leu Leu Ala Gln Gly Ile
370                 375                 380
Val Val Asp Trp Gln Pro Ala Leu Arg Leu Pro Trp Val Met Gly Gly
385                 390                 395                 400
Glu Ser Ser Leu Arg Ser Met Ile Lys His Leu Val Asp Asn Ala Ile
            405                 410                 415
Glu Ser Met Ser Gln Asn Gln Val Ser Arg Arg Glu Leu Phe Ile Ser
        420                 425                 430
Thr Arg Val Glu Asn His Leu Val Arg Met Glu Ile Thr Asp Ser Gly
    435                 440                 445
Pro Gly Ile Pro Pro Asp Leu Val Leu Lys Val Phe Glu Pro Phe Phe
450                 455                 460
Ser Thr Lys Pro Pro His Arg Val Gly Arg Gly Met Gly Leu Pro Val
465                 470                 475                 480
Val Gln Glu Ile Val Ala His Ala Gly Met Val His Val Asp Thr Asp
            485                 490                 495
Tyr Arg Glu Gly Cys Arg Ile Val Val Glu Leu Pro Phe Ser Ala Ser
        500                 505                 510
Thr
```

<210> SEQ ID NO 3
<211> LENGTH: 1417
<212> TYPE: DNA
<213> ORGANISM: Azotobacter chroococcum CBD15

<400> SEQUENCE: 3

```
atcgcgcttt ccgcaccatc accggctacg gcagcgagga agtgctcggc aagaacgaat      60
cgatcctctc caacggcacc acgccgcgcc tggtctacca ggcccgtgtg ggctggctgg     120
cgcagaagaa gccctggtcc ggcgtgctgg tcaaccgccg caaggacaag accctgtacc     180
tggccgaact gaccgtggcg ccggtgctca acgaggccgg cgagaccatc tactacctgg     240
gcatgcaccg cgacaccagc gaattgcacg aactggaaca acgcgtcaac aaccagcgcc     300
tgatgatcga ggcggtggtc agcgccgccc ggcggcgat ggtggtgctc gaccgccagc     360
accgggtgat gctctccaac ccgagcttct gccgcctggc ccgcgacctg gtcgaggatg     420
gcagcagcga gagcctggtg gcgctgctgc gggaaaacct cgccgccccc ttcgagacgc     480
tggaaaacca gggcagcgcc ttctccggca aggagatctc cttcgacctg gcggccgct      540
cgccgcgctg gctgtcctgc cacggccggg ccatccacat cgagaacgag caggcccacg     600
tgttcttcgc gcccaccgag gaacgctacc ctgctgctga ccatcaacga catctccgag     660
ctgcgccaga gcagcagga ttcgcggctc aacgcgctga aggcgctgat ggccgaggaa     720
gagctgctgg aaggcatgcg cgagaccttc aacgccgcca tccatcgcct gcagggcccg     780
gccaacctga tcagcgcggc gatgcgcatg ctcgaacggc gcctcggcgg caaggccggc     840
aacgacccgg tgctgagcgc catgcgcgaa ccagcacgg ccggaatgga ggcactggag     900
aacctcagtg gctccattcc ggtgcgcatg gccgagtcca agatgccggt caacctcaac     960
cagttgatcc gcgaggtgat caccctgtgc accgaccagt tgctggccca gggcatcgtc    1020
```

```
gtcgactggc agccggcgct gcgcctgccc tgggtgatgg gcggggaaag cagcctgcgc   1080
agcatgatca agcacctggt cgacaacgcc atcgagtcca tgagccagaa ccaggtcagc   1140
cgccgcgagc tgttcatcag cacccgcgtg gagaaccacc tggtgcgcat ggagatcacc   1200
gacagcggcc cgggcattcc gcccgacctg gtgctgaagg tgttcgagcc gttcttcagc   1260
accaagccgc acaccgcgt cggggcgcggc acgggcctgc cggtggtgca ggagatcgtc   1320
gccaagcacg ccggcatggt gcacgtagac accgactatc gggaaggctg ccggatcgtc   1380
gtcgagctgc ccttctcggc ctcacctcta gagtcga                            1417
```

<210> SEQ ID NO 4
<211> LENGTH: 1569
<212> TYPE: DNA
<213> ORGANISM: Azotobacter vinelandii

<400> SEQUENCE: 4

```
atgaatgcaa ccatccctca gcgctcggcc aaacagaacc cggtcgaact ctatgacctg     60
caattgcagg ccctggcgag catcgcccgc acgctcagcc gcgaacaaca gatcgacgaa    120
ctgctcgaac aggtcctggc cgtactgcac aatgacctcg gcctgctgca tggcctggtg    180
accatttccg acccggaaca cggggccctg cagatcggcg ccatccacac cgactcggaa    240
gcggtggccc aggcctgcga aggcgtgcgc tacagaagcg gcgaagggggt gatcggcaac    300 gtgctcaagc acggcaacag cgtggtgctc gggcgcatct ccgccgaccc gcgctttctc    360
gaccgcctgg cgctgtacga cctggaaatg ccgttcatcg gggtgccgat caagaacccc    420
gagggcaaca ccatcggcgt gctggcggcc cagccggact gccgcgccga cgagcacatg    480
cccgcgcgca cgcgcttcct ggagatcgtc gccaacctgc tggcgcagac cgtgcgcctg    540
gtggtgaaca tcgaggacgg ccgcgaggcg ccgacgagc gcgaggaact cgtcgcgag    600 gtgcgcggca gtacggcctt cgagaacatg gtggtgggcc acacccccac catgcgccgg    660
gtgttcgatc agatccgccg ggtcgccaag tggaacagca ccgtactggt cctcggcgag    720
tccggtaccg gcaaggaact gatcgccagc gccatccact acaagtcgcc gcgcgcgcac    780
cgccccttcg tccgcctgaa ctgcgccgcg ctgccggaaa ccctgctcga gtccgaactc    840
ttcggccacg agaagggcgc cttcaccggc gcggtgaagc agcgcaaggg gcgtttcgag    900
caggccgacg gcggcaccct gttcctcgac gagatcggcg agatctcgcc gatgttccag    960
gccaagctgc tgcgcgtgct gcaggaaggc gagttcgagc gggtcggcgg caaccagacg   1020
gtgcgggtca acgtgcgcat cgtcgccgcc accaaccgcg acctggaaag cgaggtggaa   1080
aagggcaagt ccgcgagga cctctactac cgcctgaacg tcatggccat ccgcattccg   1140
ccgctgcgcg agcgtaccgc cgacattccc gaactggcgg aattcctgct cggcaagatc   1200
ggccgccagc agggccgccc gctgaccgtc accgacagcg ccatccgcct gctgatgagc   1260
caccgctggc cgggcaacgt gcgcgaactg gagaactgcc tggagcgctc ggcgatcatg   1320
agcgaggacg gcaccatcac ccgcgacgtg gtctcgctga ccggggtcga caacgagagc   1380
ccgccgctcg ccgcgccgct gcccgaggtc aacctggccg acgagaccct ggacgaccgc   1440
gaacgggtga tcgccgccct cgaacaggcc ggctgggtgc aggccaaggc cgcgcggctg   1500
ctgggcatga cgccgcggca gatcgcctac cgcatccaga ccctcaacat ccacatgcgc   1560
aagatctga                                                           1569
```

<210> SEQ ID NO 5

<211> LENGTH: 519
<212> TYPE: PRT
<213> ORGANISM: Azotobacter vinelandii

<400> SEQUENCE: 5

```
Met Asn Ala Thr Ile Pro Gln Arg Ser Ala Lys Gln Asn Pro Val Glu
1               5                   10                  15

Leu Tyr Asp Leu Gln Leu Gln Ala Leu Ala Ser Ile Ala Arg Thr Leu
            20                  25                  30

Ser Arg Glu Gln Gln Ile Asp Glu Leu Leu Glu Gln Val Leu Ala Val
        35                  40                  45

Leu His Asn Asp Leu Gly Leu Leu His Gly Leu Val Thr Ile Ser Asp
    50                  55                  60

Pro Glu His Gly Ala Leu Gln Ile Gly Ala Ile His Thr Asp Ser Glu
65                  70                  75                  80

Ala Val Ala Gln Ala Cys Glu Gly Val Arg Tyr Arg Ser Gly Glu Gly
                85                  90                  95

Val Ile Gly Asn Val Leu His Gly Asn Ser Val Val Leu Gly Arg Ile
            100                 105                 110

Ser Ala Asp Pro Arg Phe Leu Asp Arg Leu Ala Leu Tyr Asp Leu Glu
        115                 120                 125

Met Pro Phe Ile Ala Val Pro Ile Lys Asn Pro Glu Gly Asn Thr Ile
    130                 135                 140

Gly Val Leu Ala Ala Gln Pro Asp Cys Arg Ala Asp Glu His Met Pro
145                 150                 155                 160

Ala Arg Thr Arg Phe Leu Glu Ile Val Ala Asn Leu Leu Ala Gln Thr
                165                 170                 175

Val Arg Leu Val Val Asn Ile Glu Asp Gly Arg Glu Ala Ala Asp Glu
            180                 185                 190

Arg Asp Glu Leu Arg Arg Glu Val Arg Gly Tyr Gly Phe Glu Asn Met
        195                 200                 205

Val Val Gly His Thr Pro Thr Met Arg Arg Val Phe Asp Gln Ile Arg
    210                 215                 220

Arg Val Ala Lys Trp Asn Ser Thr Val Leu Val Leu Gly Glu Ser Gly
225                 230                 235                 240

Thr Gly Glu Leu Ile Ala Ser Ala Ile His Tyr Lys Ser Pro Arg Ala
                245                 250                 255

His Arg Pro Phe Val Arg Leu Asn Cys Ala Ala Leu Pro Glu Thr Leu
            260                 265                 270

Leu Glu Ser Glu Leu Phe Gly His Glu Lys Gly Ala Phe Thr Gly Ala
        275                 280                 285

Val Lys Gln Arg Lys Gly Arg Phe Glu Gln Ala Asp Gly Gly Thr Leu
    290                 295                 300

Phe Leu Asp Glu Ile Gly Glu Ile Ser Pro Met Phe Gln Ala Lys Leu
305                 310                 315                 320

Leu Arg Val Leu Gln Glu Gly Glu Phe Glu Arg Val Gly Gly Asn Gln
                325                 330                 335

Thr Val Arg Val Asn Val Arg Ile Val Ala Ala Thr Asn Arg Asp Leu
            340                 345                 350

Glu Ser Glu Val Glu Lys Gly Lys Phe Arg Glu Asp Leu Tyr Tyr Arg
        355                 360                 365

Leu Asn Val Met Ala Ile Arg Ile Pro Pro Leu Arg Glu Arg Thr Ala
    370                 375                 380

Asp Ile Pro Glu Leu Ala Glu Phe Leu Leu Gly Lys Ile Gly Arg Gln
```

```
                385                 390                 395                 400

Gln Gly Arg Pro Leu Thr Val Thr Asp Ser Ala Ile Arg Leu Leu Met
            405                 410                 415

Ser His Arg Trp Pro Gly Asn Val Arg Glu Leu Glu Asn Cys Leu Glu
            420                 425                 430

Arg Ser Ala Ile Met Ser Glu Asp Gly Thr Ile Thr Arg Asp Val Val
            435                 440                 445

Ser Leu Thr Gly Val Asp Asn Glu Ser Pro Pro Leu Ala Ala Pro Leu
            450                 455                 460

Pro Glu Val Asn Leu Ala Asp Glu Thr Leu Asp Asp Arg Glu Arg Val
465                 470                 475                 480

Ile Ala Ala Leu Glu Gln Ala Gly Trp Val Gln Ala Lys Ala Ala Arg
                485                 490                 495

Leu Leu Gly Met Thr Pro Arg Gln Ile Ala Tyr Arg Ile Gln Thr Leu
            500                 505                 510

Asn Ile His Met Arg Lys Ile
            515

<210> SEQ ID NO 6
<211> LENGTH: 383
<212> TYPE: DNA
<213> ORGANISM: Azotobacter

<400> SEQUENCE: 6
gaattctcat gtttgacagc ttatcatcga ttagctttaa tgcggtagtt tatcacagtt      60
aaattgctaa cgcagtcagg caccgtgtat gaaatctaac aatgcgctca tcgtcatcct     120
cggcaccgtc accctggatg ctgtaggcat aggcttggtt atgccggtac tgccgggcct     180
cttgcgggat atcgtccatt ccgacagcat cgccagtcac tatggcgtgc tgctagcgct     240
atatgcgttg atgcaatttc tatgcgcacc cgttctcgga gcactgtccg accgctttgg     300
ccgccgccca gtdcctgctc gcttcgctac ttggagccac tatcactacg cgatcatggc     360
gaccacaccc gtcctgtgga tcc                                              383
```